US007732147B2

(12) United States Patent
Vincent et al.

(10) Patent No.: US 7,732,147 B2
(45) Date of Patent: *Jun. 8, 2010

(54) NEUROTRANSMISSION DISORDERS

(75) Inventors: Angela Vincent, Oxford (GB); Werner Hoch, Houston, TX (US)

(73) Assignees: Isis Innovation Limited, Oxford (GB); Max-Planck Gesellschaft zur Foerderung der Wissenschaften E.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/895,793

(22) Filed: Aug. 27, 2007

(65) Prior Publication Data

US 2008/0057524 A1 Mar. 6, 2008

Related U.S. Application Data

(63) Continuation of application No. 10/311,575, filed as application No. PCT/GB01/02661 on Jun. 15, 2001, now Pat. No. 7,267,820.

(30) Foreign Application Priority Data

Jun. 16, 2000 (GB) ................................. 0014878.3

(51) Int. Cl.
 *G01N 33/53* (2006.01)
 *C07K 14/00* (2006.01)
 *C07K 16/00* (2006.01)
 *C12P 21/08* (2006.01)

(52) U.S. Cl. .......................... 435/7.1; 435/7.2; 530/350; 530/387.1; 530/388.1

(58) Field of Classification Search ........................ None
See application file for complete search history.

(56) References Cited

U.S. PATENT DOCUMENTS 5,814,478 A 9/1998 Bowen et al.
7,267,820 B2 * 9/2007 Vincent et al. ........... 424/130.1

FOREIGN PATENT DOCUMENTS

WO WO 99/10494 3/1999

OTHER PUBLICATIONS

Lueck, et al, 2007, Muscle Chloride Channel Dysfunction in Two Mouse Models of Myotonic Dystrophy. J. Gen. Physiol., 129(1): 79-94.*
Meinen, et al, 2007. Linker molecules between laminins and dystroglycan ameliorate laminin-α2—deficient muscular dystrophy at all disease stages. J. Cell Biol. 176(7): 979-993.*
Lamke, A.K. & Bushby, K.M.D., 2005, Collagen VI related muscle disorders, J. Med. Genet, 42: 673-685.*
Behin, et al, 2008, Severe neonatal myasthenia due to maternal anti-MuSK antibodies. Neuromuscular Disorders 18: 443-446.*

Blaes, F., et al., "IgG' from 'seronegative' myasthenia gravis patients binds to a muscle cell line, TE671, but not to human acetylcholine receptor," *Ann Neurol*, 47(4): 504-510 (Apr. 2000).
Brooks, E.B., et al., "A sensitive rosetting assay for detection of acetylcholine receptor antibodies using BC3H-1 cells: positive results in 'antibody-negative' myasthenia gravis," *J. Neuroimmunol.*, 28(1): 83-93 (Jun. 1990).
Drachman, D.B., "Myasthenia gravis," *N Engl J Med*, 330(25): 1797-1810 (Jun. 1994).
Glass, D.J., et al., "Agrin acts via a MuSK receptor complex," *Cell*, 85(4): 513-523 (May 1996).
Hoch, W., et al., "Auto-antibodies to the receptor tyrosine kinase MuSK in patients with myasthenia gravis without acetylcholine receptor antibodies," *Nat Med*, 7(3): 365-368 (Mar. 2001).
Hoch, W., et al., "Structural domains of agrin required for clustering of nicotine acetylcholine receptors," *EMBO J*, 13(12): 2814-2821 (Jun. 1994).
Hopf, C., et al., "Heparin inhibits acetylcholine receptor-aggregation of two distinct steps in the agrin-induced pathway," *Eur J Neurosci*, 9(6):1170-1177 (Jun. 1997).
Hopf, C., et al., "Dimerization of the muscle-specific kinase induces tyrosine phosphorylation of acetylcholine receptors and their aggregation on the surface of myotubes," *J Biol Chem*, 273(11): 6467-6473 (Mar. 1998).
Hopf, C., et al., "Tyrosine phosphorylation of the muscle-specific kinase is exclusively induced by acetylcholine receptor-aggregating agrin fragments," *Eur J Biochem*, 253(2): 382-389 (Apr. 1998).
Lindstrom, J., et al., "Antibody to acetylcholine receptor in myasthenia gravis. Prevalence, clinical correlates and diagnostic values," *Neurology*, 26(11): 1054-1059 (Nov. 1976).
Mier, A.K., et al., "Diaphragmatic myasthenia in mother and child," *Postgraduate Med J*, 611: 725-727 (1985).
Mossman, S., et al., "Myasthenia gravis without acetylcholine-receptor antibody: a distinct disease entity," *Lancet*, 1(8473): 116-119 (Jan. 1986).
Riemersma, S., et al., "Association of arthrogryposis multiplex congenita with maternal antibodies inhibiting fetal acetylcholine receptor function," *J Clin Invest*, 98(10): 2358-2363 (Nov. 1996).
Robertson, S.C., et al., "RTK mutations and human syndromes: when good receptors turn bad," *Trends Genet*, 16(6): 265-271 (Jun. 2000).

(Continued)

*Primary Examiner*—Dong Jiang
*Assistant Examiner*—Sandra Wegert
(74) *Attorney, Agent, or Firm*—Hamilton, Brook, Smith & Reynolds, P.C.

(57) ABSTRACT

There is disclosed a method for diagnosing neurotransmission or developmental disorders in a mammal comprising the step of detecting in a bodily fluid of said mammal autoantibodies to an epitope of the muscle specific tyrosine kinase (MuSK). One such method comprises a) contacting said bodily fluid with said MuSK or an antigenic determinant thereof; and b) detecting any antibody-antigen complexes formed between said receptor tyrosine kinase or an antigenic fragment thereof and antibodies present in said bodily fluid, wherein the presence of said complexes is indicative of said mammal suffering from said neurotransmission or developmental disorders. Also disclosed are kits for use in the diagnosis of neurotransmission and subsequent developmental disorders.

4 Claims, 6 Drawing Sheets

OTHER PUBLICATIONS

Sanes, J.R., et al., "Development of the vertebrate neuromuscular junction," *Annual Review of Neuroscience*, 22: 389-442 (1999).

Saunders, D.B., et al., "Seronegative myasthenia gravis," *Neurology*, 48: S40-S45 (1997).

Taylor, S.I., et al., "Syndromes of autoimmunity and hypoglycemia. Autoantibodies directed against insulin and its receptor," *Endocrinol Metab Clin North Am*, 18(1): 123-143 (Mar. 1989).

Valenzuela, D.M., et al., "Receptor tyrosine kinase specific for the skeletal muscle lineage: expression in embryonic muscle, at the neuromuscular junction, and after injury," *Neuron*, 15(3): 573-584 (Sep. 1995).

Vincent, A., et al., "Arthrogryposis multiplex congenita with maternal autoantibodies specific for a fetal antigen," *Lancet*: 346(8966): 24-25 (Jul. 1995).

Vincent, A., et al., "Acetylcholine receptor antibody as a diagnostic test for myasthenia gravis: Results in 153 validated cases and 2967 diagnostic assays," *J Neurol Neurosurg Psychiatry*, 48(12): 1246-1252 (Dec. 1985).

Plested, C.P., et al., "AChR phosphorylation and indirect inhibition of AChR function in seronegative MG," *Neurology*, 59: 1682-1688 (2002).

Yamamoto, T., et al., "Seronegative myasthenia gravis: a plasma factor inhibiting agonist-induced acetylcholine receptor function copurifies with IgM," *Ann Neurol*, 30(4): 550-557 (Oct. 1991).

Zhou, H., et al., "Distinct domains of MuSK mediate its ability to induce and to associate with postsynaptic specializations," *J Cell Biol*, 146(5): 1133-1146 (Sep. 1999).

Liyanage, Y., et al., "The agrin/muscle specific kinase pathway; new targets for autoimmune and genetic disorders at the neuromuscular junction," *Invited Review, Muscle Nerve*, 25(1): 4-16 (Jan. 2002).

Palace, J., et al., "Myasthenia gravis: diagnostic and management dilemmas," *Curr Opin Neurol*, 14(5): 583-589 (Oct. 2001).

Sanders, D.B., et al., "Clinical aspects of MuSK antibody positive seronegative MB," *Neurology*, 60(12): 1978-1980 (2003).

Vincent, A., "Unraveling the pathogenesis of myasthenia gravis," *Nat Rev Immunol*, 2(10): 797-804 (Oct. 2002).

Vincent, A., et al., "Seronegative generalized myasthenia gravis: clinical features, antibodies and their targets," *Lancet Neurology*, 2: 99-106 (2003).

Sisman, et al., *Indian Pediatrics*, 41: 938-940 (2004).

\* cited by examiner

NEUROTRANSMISSION DISORDERS

RELATED APPLICATIONS

This application is a continuation of U.S. application Ser. No. 10/311,575, with a 371(c) date of Jun. 6, 2003, now U.S. Pat. No. 7,267,820, issued on Sep. 11, 2007, which is the U.S. National Stage of International Application No. PCT/GB01/02661, filed on Jun. 15, 2001, published in English, which claims priority under 35 U.S.C. §119 or 365 to Great Britain, Application No. GB 0014878.3, filed Jun. 16, 2000. The entire teachings of the above application(s) are incorporated herein by reference.

SUMMARY OF THE INVENTION

The present invention is concerned with neurotransmission disorders and, in particular, with a method of diagnosing such disorders in mammals. Also provided by the present invention are kits for use in said diagnosis.

Myasthenia gravis (MG) is a chronic autoimmune disorder of neuromuscular transmission resulting in muscle weakness. The key feature of weakness due to MG is its variability. Patients generally experience a waning of strength throughout the day with a tendency to fatigue later in the day or even towards the end of a particular task. A symptom of MG is often ocular weakness, causing ptosis (drooping eyelids) and/or diplopia (double vision). Other symptoms include leg weakness, dysphagia and slurred or nasal speech. Symptoms of weakness tend to worsen with various stressors, such as, exertion, heat and infection.

In 1960 it was discovered that MG was caused by antibodies against the acetyl choline receptor (AChR) and that it is therefore autoimmune in origin. Today MG is one of the most characterized of neurological disorders which has consequently lead to treatments which vastly improve the length and quality of life of myasthenics. Approximately 10 people in every million of a population contract this disease in one year. There is no racial predominance and 75% of MG patients less than 40 years of age are female and 60% of those older than 40 years are male.

Approximately 80% of patients with MG possess within their plasma autoantibodies that are immunoprecitipatable with radiolabeled AChR. The remaining 20% of MG patients do not, however, exhibit such antibodies in their plasma but do have similar symptoms and respond to the same therapies such as plasma exchange and immunosuppression. Accordingly, it has not been established whether these patients have the same or a distinct and separate MG condition (3,4). Autoantibodies are naturally occurring antibodies directed to an antigen which an individual's immune response recognizes as foreign even though that antigen actually originated in the individual. They may be present in the circulatory system as circulating free antibodies or in the form of circulating immune complexes bound to their target depending on the nature of the antigen concerned.

Human plasma from patients who were anti-AChR autoantibodies negative (AAAN or previously known as sero-negative MG), were investigated for alternative autoantibodies and one candidate autoantibody was that one for the MuSK protein.

The present inventors surprisingly found that many of the 20% of MG patients which do not exhibit any autoantibodies to AChR, instead have IgG antibodies directed against the extracellular N-terminal domains of MuSK, a receptor tyrosine kinase located on the cell. surface of neuromuscular junctions, indicating that they are afflicted with a form of MG which has a different etiology from MG characterised by circulating autoantibodies to AChR.

The MuSK protein has been sequenced and the protein characterised recently by Valenzuela et al. (International patent application number PCT/US96/20696, published as WO97/21811). It is a receptor tyrosine kinase (RTK) located on the cell surface of muscle cells at the neuromuscular junction.

Ligands bind to RTKs at the binding site on the extracellular side of the receptor, which induces transmission of a signal cascade to intracellular target proteins. RTKs are classified according to their function and members of these families share high homology in their amino acid sequence as well as functionality.

At the neuromuscular junction (NMJ) where the motor nerve axon dendrites meet the muscle cell basal membrane, important physiological signals are exchanged between these adjacent cells. An example of this is the chemical transmitter acetyl choline which passes through the synaptic cleft from the nerve cell, and is then rapidly and specifically bound by the AChR at the muscle cell wall. This in turn begins a cascade of events which ultimately leads to contraction of the muscle cells.

The post synaptic structure at the muscle cell wall is termed the motor endplate which is densely packed with protein and lipid, thereby giving an electron dense appearance when observed by electron microscopy. The muscle AChRs are present here, and it is believed that signaling gives rise to concentrations of proteins there by two mechanisms; one is altered distribution of pre-existing membrane proteins and the other is by induction of localized transcription of specific genes only by subsynaptic nuclei underlying the NMJ.

Development of the neuromuscular junction is initiated through activation of MuSK. Agrin isoforms, released from the motorneuron, trigger MuSK and muscle acetylcholine receptor (AChR) phosphorylation resulting in clustering of AChRs and other proteins of the postsynaptic apparatus (1). Agrin's ability to cause AChR clustering in cultured myotubes has been shown to be inhibited by anti agrin antibodies. It is currently accepted that agrin does not bind directly to MuSK, but via a hypothetical agrin-binding component termed Myotubule Associated Specificity Component (MASC) (1,11). No disease associated with either MuSK, MASC, or agrins has been reported and their roles in adult muscle have not yet been elucidated.

It has already been shown that anti AChR autoantibody negative MG is caused by humoral IgG antibodies: it can be successfully treated by plasma exchange and other immune therapies (5); transient neonatal MG was reported in the newborn infant of one of the patients with anti-MuSK antibodies (17); and injection of immunoglobulin or IgG preparations into mice caused defects in neuromuscular transmission (5).

The present inventors have therefore now shown that anti-MuSK antibodies have functional effects on agrin-induced AChR clustering in vitro, and direct interference with this agrin/MuSK/AChR pathway may be an important disease mechanism in vivo. MuSK is a relatively new member of the receptor tyrosine kinase (RTK) family. With very few exceptions (for example, see 18), autoantibodies to RTKs have not been implicated in human disorders but the combination of large extracellular domains and functional activities make them attractive potential antigens in other autoimmune conditions. Other members of the RTK family are mutated in inherited diseases, and somatic mutations have been found in various tumors (19). MuSK may prove to be involved in congenital as well as acquired muscle disorders.

Therefore, there is provided by a first aspect of the present invention a method of diagnosing neurotransmission disorders in a mammal comprising the step of detecting in a bodily fluid of said mammal autoantibodies to an epitope of the muscle specific tyrosine kinase, MuSK.

More specifically the neurotransmission disorder will preferably be Myasthenia gravis and more particularly a subclass or subtype of MG which is generally found in patients who do not exhibit the ability to immunoprecipitate radiolabeled AChR with their bodily fluids.

This aspect of the invention is particularly advantageous because the identification of this new subclass or subtype of MG patients will allow for more accurate and speedy diagnosis of individuals by medical practitioners. The method according to this aspect of the invention will allow for detection of neurotransmission abnormalities that are either congenital or acquired, for example, postnatally or prenatally from transmission from the mother to the fetus. As set out in more detail in the example provided, some mothers of babies with developmental disorders, such as paralysis and fixed joints were identified as having antibodies to MuSK, which were transferred placentally.

Until now, MuSK has been studied primarily in NMJ development. The presence of antibodies to the extracellular domain of MuSK in an acquired disorder implies that MuSK is functional at the adult NMJ, and implicates MuSK as a novel target for pathogenic autoantibodies causing Myasthenia gravis. The isolation and purification of this anti-MUSK autoantibody will give rise to a useful product which may be exploitable as an indicator of neurotransmission diseases.

Preferably, the method according to the first aspect of the invention, comprises the steps of a) contacting said bodily fluid with said MuSK or an antigenic determinant thereof; and b) detecting any antibody-antigen complexes formed between said MuSK or an antigenic fragment thereof and antibodies present in said bodily fluid, wherein the presence of said complexes is indicative of said mammal suffering from said neurotransmission disorders.

The actual steps of detecting autoantibodies in a sample of bodily fluids may be performed in accordance with immunological assay techniques known per se in the art. Examples of suitable techniques include ELISA, radioimmunoassays and the like. In general terms, such assays use an antigen which may be immobilized on a solid support. A sample to be tested is brought into contact with the antigen and if autoantibodies specific to the protein are present in a sample they will immunologically react with the antigen to form autoantibody-antigen complexes which may then be detected or quantitatively measured. Detection of autoantibody-antigen complexes is preferably carried out using a secondary anti-human immunoglobulin antibody, typically anti-IgG or anti-human IgM, which recognizes general features common to all human IgGs or IgMs, respectively. The secondary antibody is usually conjugated to an enzyme such as, for example, horseradish peroxidase (HRP) so that detecting of autoantibody/antigen/secondary antibody complexes is achieved by addition of an enzyme substrate and subsequent calorimetric, chemiluminescent or fluorescent detection of the enzymatic reaction products.

Thus, in one embodiment the antibody/antigen complex may be detected by a further antibody, such as an anti-IgG antibody. Complexes may alternatively be viewed by microscopy. Other labels or reporter molecules which may be used in a method according to the invention. Preferably, said reporter molecule or label includes any of a heavy metal, a fluorescent or luminescent molecule, radioactive or enzymatic tag. Preferably, the label or reporter molecule is such that the intensity of the signal from the anti-human IgG antibody is indicative of the relative amount of the anti-MuSK autoantibody in the bodily fluid when compared to a positive and negative control reading.

An alternative method of detecting autoantibodies for MuSK or an epitope thereof relies upon the binding of a MuSK or its epitope, together with a revealing label, to the autoantibodies in the serum or bodily fluid. This method comprises contacting MuSK or an epitope or antigenic determinant thereof having a suitable label thereon, with said bodily fluid, immunoprecipitating any antibodies from said bodily fluid and monitoring for said label on any of said antibodies, wherein the presence of said label is indicative of said mammal suffering from said neurotransmission or developmental disorder. Preferably, the label is a radioactive label which may be I, or the like. Iodination and immunoprecipitation are standard techniques in the art, the details of which may be found in references (4 and 6).

In a further aspect of the invention, there is provided an assay kit for diagnosing neurotransmission disorders in mammals comprising an epitope of muscle specific tyrosine kinase (MuSK) and means for contacting said MuSK with a bodily fluid from a mammal. Thus advantageously, an assay system for detecting neurotransmission disorders, and particularly Myasthenia gravis in patients who are anti-AChR autoantibody negative (AAAN) is provided. Prior to the present invention there was no basis for providing an immediate clinical diagnosis for such patients.

Also provided by the invention is an isolated or purified autoantibody specific for MuSK. Such an antibody can be detected in bodily fluids of mammals and isolated or purified therefrom using techniques which would be known to the skilled practitioner, such as, immunoabsorption, or immunoaffinity chromatography or high pressure chromatography.

In a further aspect the invention also comprises an isolated or purified antibody specific for an anti-MuSK autoantibody from bodily fluid of a mammal. Such a purified or isolated antibody which is specific for anti-MuSK autoantibody may advantageously be used as a medicament, or in the preparation of a medicament for treating neurotransmission disorders in a mammal, and preferably a human suffering from Myasthenia gravis. Such an antibody may also be included in a pharmaceutical composition together with a pharmaceutically acceptable carrier, excipient or diluent therefor. Antibodies, polyclonal or monoclonal may be prepared using techniques which are known in the art. For example, the technique described by Kohler & Milstein (1975, *Nature* 256: 495-497) for developing hybridomas capable of producing monoclonal antibodies may be used. Monoclonal antibodies for therapeutic use may be human monoclonal antibodies or chimeric human-mouse monoclonal antibodies. Chimeric antibody molecules may be prepared containing a mouse antigen binding domain with human constant regions (Morrison et al., 1984, *Proc. Natl. Acad. Sci. USA* 81: 6581, Takeda et al., 1985, *Nature* 314: 452). For production of antibody various host animals can be immunized by injection with anti-MuSK autoantibody, or a fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

The present invention includes not only complete antibody molecules but fragments thereof. Antibody fragments which contain the idiotype of the molecule can be generated by known techniques, for example, such fragments include but are not limited to the F (ab')$_2$ fragment which can be produced by pepsin digestion of the antibody molecule; the Fab' fragments which can be generated by reducing the disulfide bridges of the F (ab')$_2$ fragments and the Fab fragments which can be generated by treating the antibody molecule with papain and a reducing agent.

The antibody which is specific for anti-MuSK autoantibodies may also, advantageously, be used in a diagnostic kit for detecting neurotransmission disorders, such as Myasthenia gravis. As aforementioned any protein which binds to the autoantibody may also be used such as an epitope or fragment of the MuSK protein itself. Such a kit comprises an isolated or purified antibody specific for anti-MuSK autoantibody according to the invention and means for contacting said antibody with a bodily fluid of a said mammal.

In accordance with the present invention a bodily fluid should be taken to mean plasma, serum, whole blood, urine, sweat, lymph, faeces, cerebrospinal fluid or nipple aspirate. In general, however, the methods of the invention will be performed on samples of serum or plasma.

In the pharmaceutical composition of the invention, preferred compositions include pharmaceutically acceptable carriers including, for example, non-toxic salts, sterile water or the like. A suitable buffer may also be present allowing the compositions to be lyophilized and stored in sterile conditions prior to reconstitution by the addition of sterile water for subsequent administration. The carrier can also contain other pharmaceutically acceptable excipients for modifying other conditions such as pH, osmolarity, viscosity, sterility, lipophilicity, solubility or the like. Pharmaceutical compositions which permit sustained or delayed release following administration may also be used.

The antibody or the MuSK protein or fragment thereof or the pharmaceutical composition of the invention may be administered orally. In this embodiment the antibody, MuSK or its eptopic fragment, or pharmaceutical composition of the invention may be encapsulated and/or combined with suitable carriers in solid dosage forms which would be well known to those of skill in the art.

Furthermore, as would be appreciated by the skilled practitioner, the specific dosage regime may be calculated according to the body surface area of the patient or the volume of body space to be occupied, dependent on the particular route of administration to be used. The amount of the composition actually administered will, however, be determined by a medical practitioner based on the circumstances pertaining to the disorder to be treated, such as the severity of the symptoms, the age, weight and response of the individual.

In a further aspect, the present invention comprises a method of treating a patient suffering from a neurotransmission disorder such as Myasthenia gravis comprising administering to said patient an effective amount of an antibody according to the invention or a MuSK protein or an epitope thereof.

In an even further aspect, the invention comprises a method for making a pharmaceutical formulation for the treatment of neurotransmission disorders, comprising the steps of isolating or purifying an antibody or MuSK protein or fragment thereof according to the invention, manufacturing bulk quantities of said antibody and formulating the antibody in a compound including a pharmaceutically acceptable carrier, diluent or excipient therefor.

In an even further aspect, the invention comprises a method of identifying compounds capable of alleviating or treating neurotransmission disorders, comprising the steps of contacting a candidate compound in the presence of MuSK or an epitope thereof and an antibody capable of binding MuSK, wherein a compound that prevents binding of said antibody to MuSK or an epitope thereof is a candidate for treating neurotransmission disorders. Such compounds may also be used in treating neurotransmission or developmental disorders or in the manufacture of a medicament for treating such disorders. The compounds identified may also, as would be appreciated by those of skill in the art, serve as lead compounds for the development of analogue compounds. The analogues should have a stabilized electronic configuration and molecular conformation that allows key functional groups to be presented to the polypeptides of the invention in-substantially the same way as the lead compound. In particular, the analogue compounds have spatial electronic properties which are comparable to the binding region, but can be smaller molecules than the lead compound, frequently having a molecular weight below about 2 kD and preferably below about 1 kD. Identification of analogue compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used.

BRIEF DESCRIPTION OF THE DRAWINGS

The present invention may be more clearly understood with reference to the following examples and accompanying Figures wherein.

Figure 1:
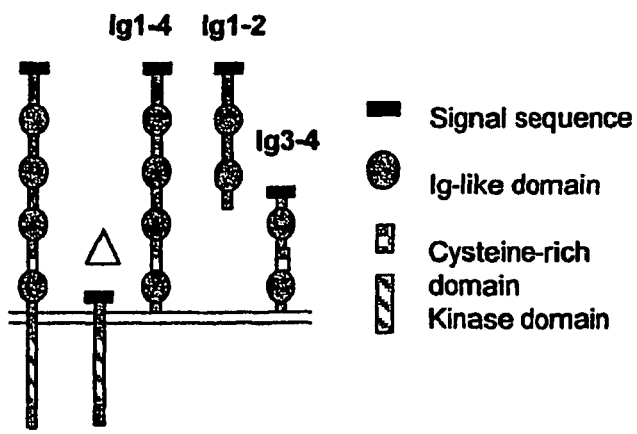
FIG. 1 is an illustration of the results obtained using antibodies from AAAN patients reacting with the extracellular domain of MuSK. Samples from AAAN patients are indicated as SNMG (sero-negative MG) as it was previously known.
Figure 1:
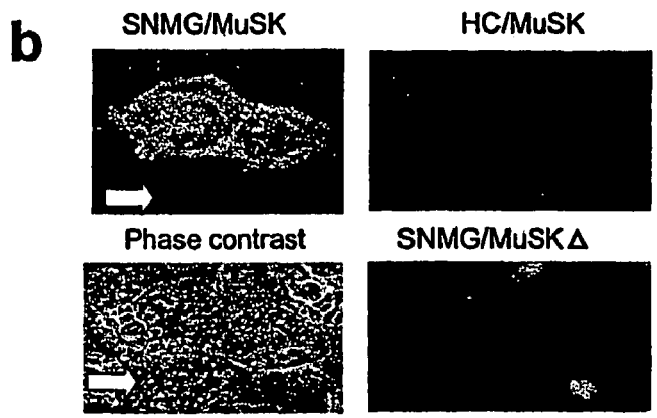
Figure 1:
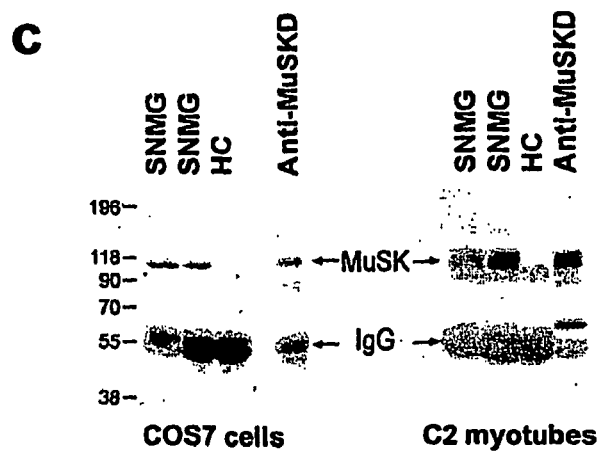

a) The MuSK constructs used are shown in FIG. 1a.

b) AAAN plasmas bound to COS-cells expressing full length MuSK (AAAN/MuSK). MuSK immunoreactivity appeared as a speckled pattern, similar to that seen previously with rabbit anti-MuSK antibodies (13). Non-transfected cells in the same field, demonstrated below by phase contrast microscopy (arrows), showed non-specific binding only. There was no specific binding of AAAN plasmas to cells expressing MuSK lacking the extracellular domains (MuSK D) or binding of healthy control plasma (HC/MuSK).

c) Two AAAN plasmas, but not a healthy control plasma, immunoprecipitated MuSK from detergent extracts of COS-cells expressing MuSK, and C2C12 myotubes. MuSK was identified by binding of an affinity-purified rabbit anti-MuSK. It appears as a 110 kD band from COS-cells and as several bands representing different MuSK splice variants in the C2C12 cells.

Figure 2:
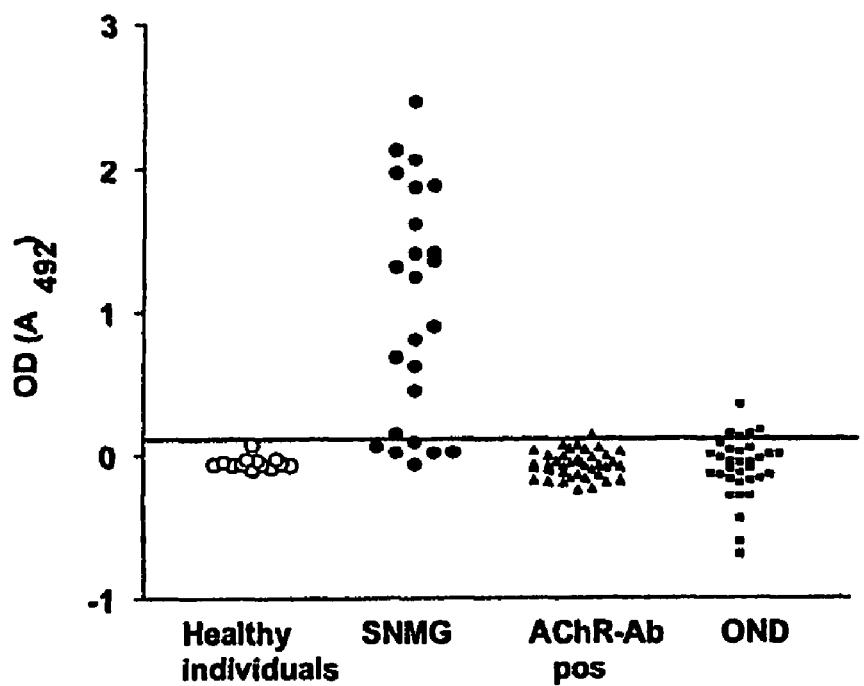
Figure 2:
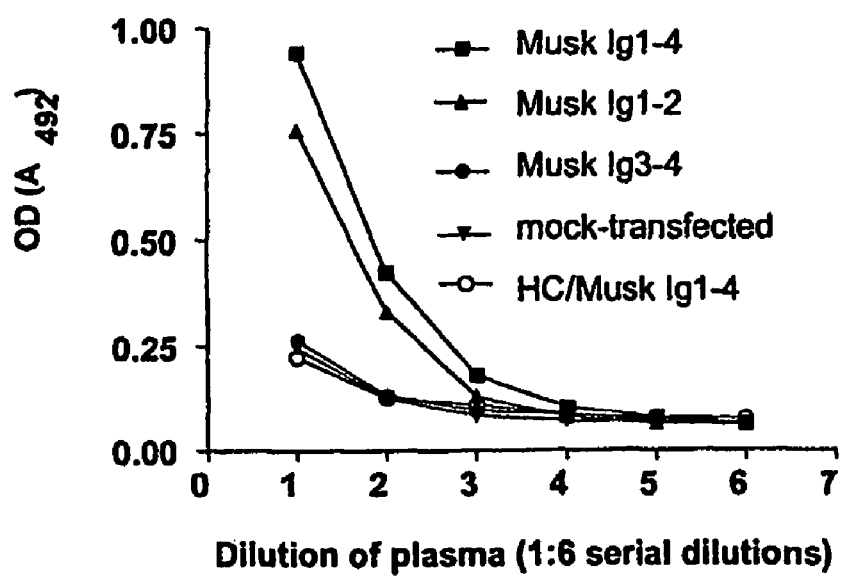

FIG. 2 is an illustration of results obtained by using IgG antibodies to the extracellular domains of MuSK in seronegative MG measured by ELISA. a, Anti-MuSK antibodies were found in 17/24 AAAN patients compared with 13 controls. Negative or borderline values only were found in 39 anti-AChR positive MG patients. Non-specific binding of IgG to the plates has been subtracted. b, Titration of one AAAN plasma against different domains of MuSK. The antibodies bound strongly to MuSK constructs expressing the distal immunoglobulin like domains, Igl-4 and Igl-2 (see FIG. 1a), but not to the Ig3-4 membrane-proximal domains.

Figure 3:
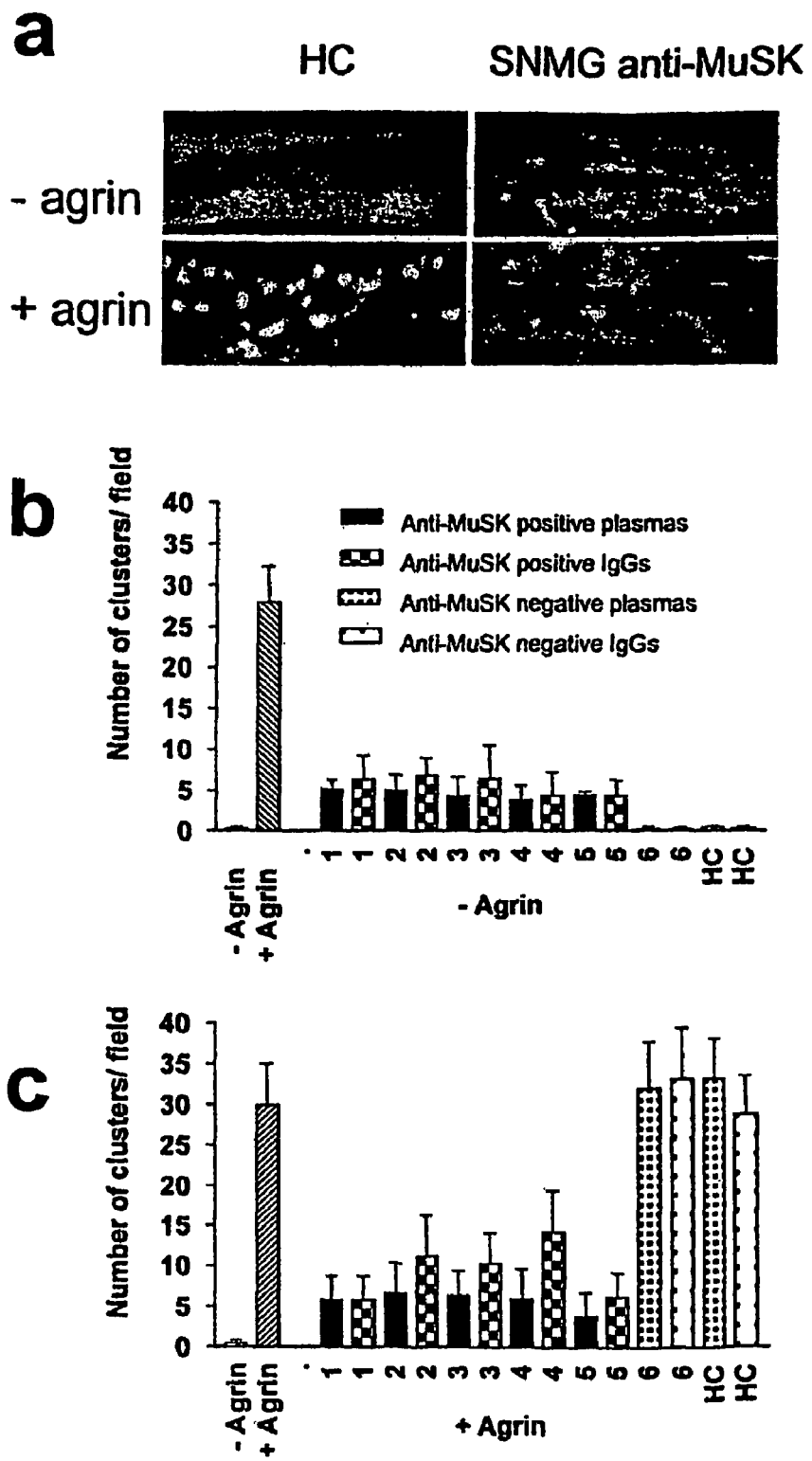

FIG. 3 is an illustration of the results that show that AAAN antibodies induce AChR clusters but inhibit agrin-induced AChR clustering.

a) In the absence of agrin, a moderate number of AChR clusters (as demonstrated by rhodamine-a-bungarotoxin fluorescence) were induced in-the presence of AAAN plasma compared to that in control plasma (HC). Agrin-induced clusters were found in the presence of healthy control plasma but were inhibited in the presence of AAAN plasma.

b), c) The AChR clusters without (b) or with (c) added agrin in plasma and IgG treated cultures. AAAN samples are labeled 1-6. Only the anti-MuSK positive plasmas and IgG preparations affected AChR clusters.

Figure 4:
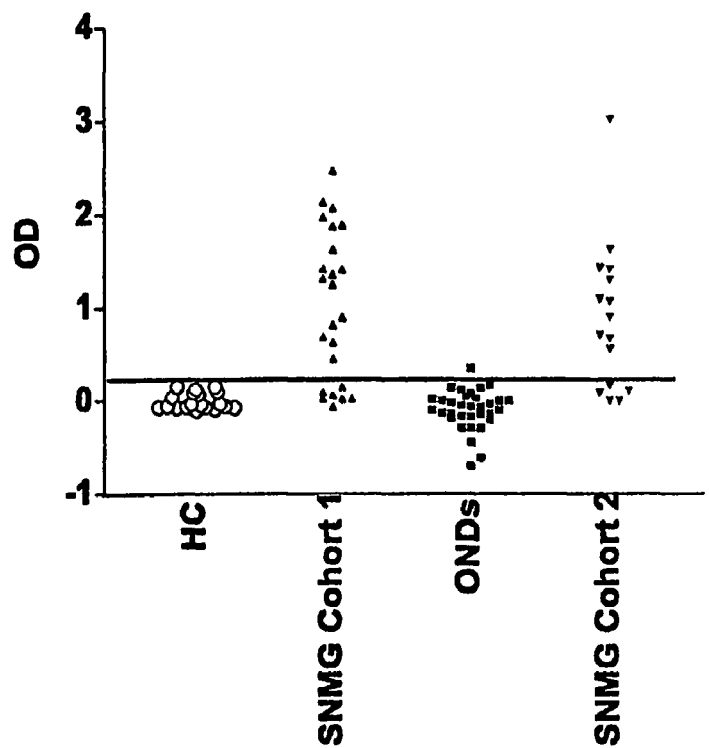

FIG. 4 is an illustration of the results obtained from further tests to confirm the specificity of the test for Myasthenia gravis set out in the examples provided.

Figure 5:
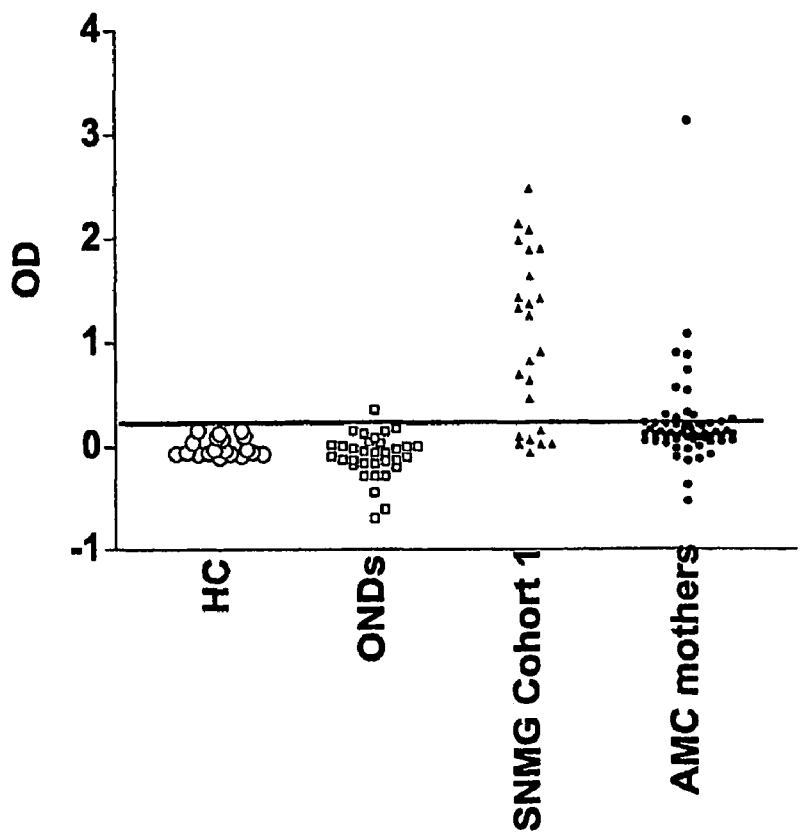

FIG. 5 is an illustration of the results obtained from a test to detect MuSK antibodies in mothers of babies with development defects.

Figure 6:
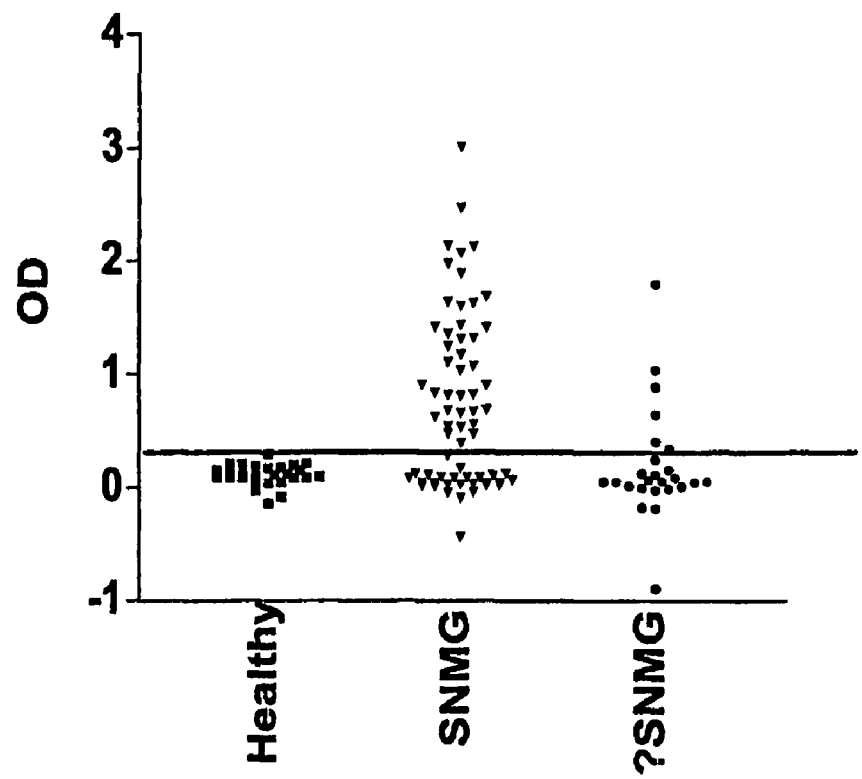

FIG. 6 is an illustration of the results obtained using an ELISA assay to detect MuSK antibodies in sera sent for analysis.

Figure 7:
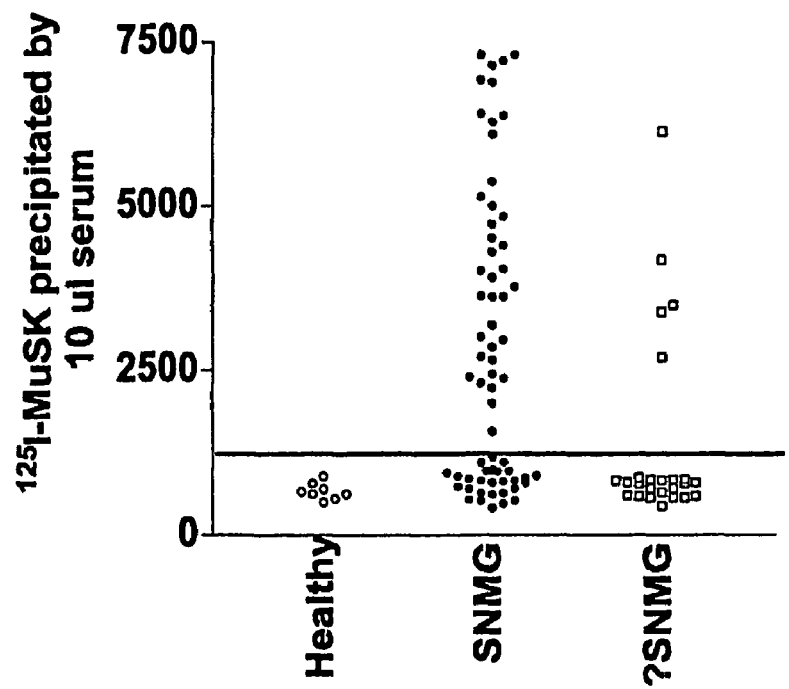

FIG. 7 is an illustration of the results obtained using an immunoprecipitation assay to detect MuSK antibodies in the sera of FIG. 6.

Figure 8:
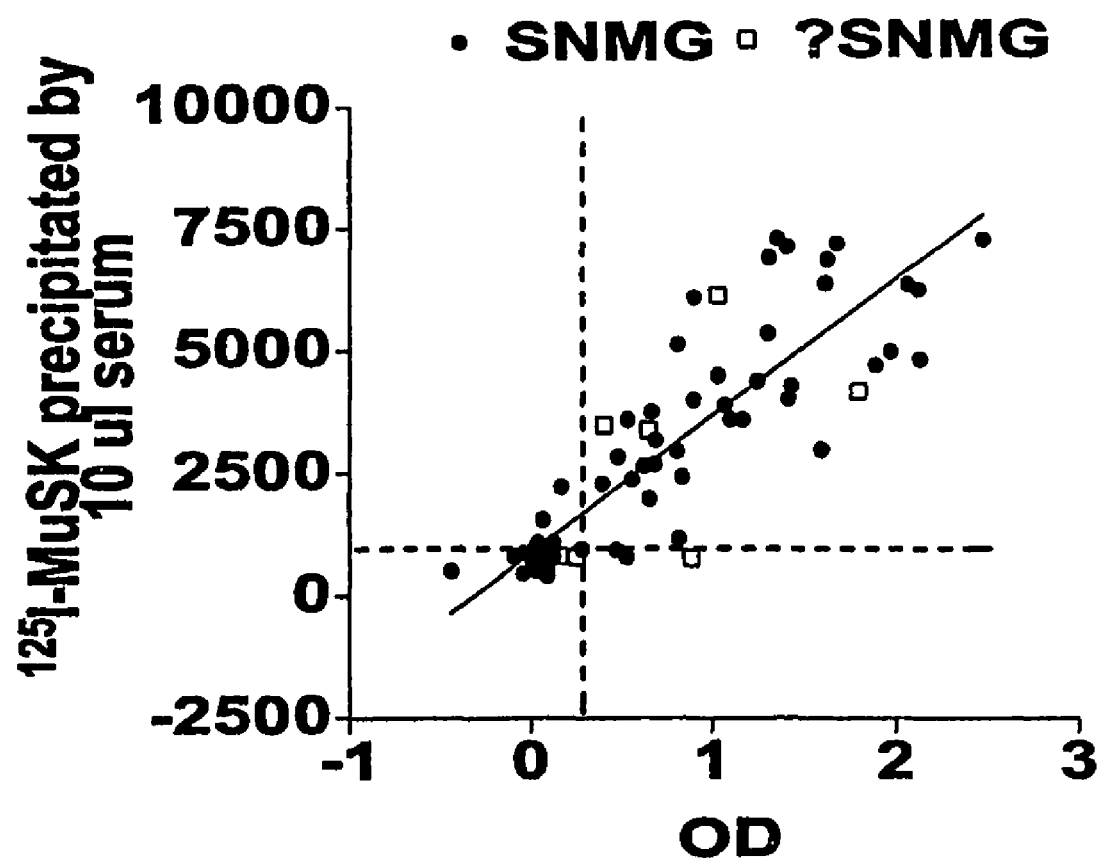

FIG. 8 is correlation of the results of ELISA and immunoprecipitation assays of FIGS. 6 and 7 for detection of MuSK antibodies.

DETAILED DESCRIPTION OF THE INVENTION

A description of example embodiments of the invention follows.

EXAMPLE

Patient Identification

Samples were obtained from 24 patients (18F, 6 M) with moderate or severe generalized MG, diagnosed by clinical electrophysiology, but in whom the standard radioimmunoprecipitation assay for anti-AChR antibodies (4) was negative on several occasions. The age at onset ranged between 2 and 68 years (median 24) and the duration of symptoms at sampling was between one month and 13 years (median 1.0 year). In 18 cases, plasma was obtained during therapeutic plasmapheresis which improved muscle strength. The remaining 6 samples were sera taken on first examination. Six of the patients had received corticosteroids for up to two months before sampling. Sera or plasmas were also obtained from healthy volunteers and from patients with anti-AChR antibody positive MG. IgG preparations were made using a Pierce ImmunoPureO (G) IgG purification kit.

MuSK and Agrin Expression Constructs.

Constructs encoding full length MuSK (13) and the soluble fragment s-agrin (4/19) (20) have been described previously. MuSK deletion fragments comprising the entire extracellular domain (Igl-4; aa 1-490, numbers according to ref (10)) or the first half encomprising two Ig-domains (Igl-2; aa 1-230) were generated by insertion of artificial stop signals at these positions. N-terminal fragments of MuSK comprising the membrane-proximal extracellular domains, including Ig-domains 3 and 4 (Ig3-4; aa 198-430), or the transmembrane region and intracellular domain (MuSK D, aa 491-869) were generated. The corresponding c-DNA-fragments, including a newly introduced SphI-site, were linked to a vector containing an artificial signal sequence followed by six histidines and a 10aa epitope-tag (20). All constructs were transiently transfected into COS7 cells (12). For the production of soluble agrin and MuSK constructs, cells were switched to serum-free medium the second day after transfection. Conditioned media, containing MuSK or agrin fragments were removed 24 hours later and analyzed by Western blotting to confirm expression.

Immunostaining of MuSK-Transfected COS7 Cells.

COS7 cells were plated onto chamber slides the day after transfection. Two days later, cells were fixed with 2% paraformaldehyde and stained as described (13). Plasmas of myasthenia gravis patients and controls were analyzed in various dilutions (between 1:20 and 1:5000). Bound antibodies were visualized with secondary antibodies conjugated to Cy3 (anti-human IgG, Dianova). In all experiments, expression of transfected MuSK constructs was confirmed by staining parallel slides with rabbit-anti MuSK antibodies (13).

Immunoprecipitation Experiments.

Detergent extracts were prepared from MuSK-transfected COS7 cells or from C2C12 myotubes that had been fused for five days. The immunoprecipitation was performed as described previously (12,13). AAAN and control plasmas incubated with the extracts at 1:20. Rabbit anti-MuSK serum was used at 1:100. MuSK in the immunoprecipitates was analysed by Western blotting using affinity-purified serum antibodies directed against the a MuSK cytoplasmic sequence (13).

ELISA Detection of Anti-MuSK Antibodies.

Conditioned medium from MuSK-transfected'COS-cells or from control cells mock-transfected with fish sperm DNA, was diluted 1:1 with 100 mM NaHC03-buffer, pH 9.5 and applied overnight to ELISA plates. Plasmas were first tested at 1:5 in triplicates and subsequently at 1:10 in duplicates. Bound antibodies were detected by horse radish peroxidase-protein A (Amersham) followed by o-phenylenediamine and measuring A492. For each sample, nonspecific immunoreactivity, determined by incubation of plates coated with conditioned medium from mock-transfected COS7 cells, was subtracted.

AChR Aggregation Assay.

The mouse muscle cell line, C2C12, was used to determine functional effects of antibodies. Cells were plated onto chamber slides, fused and treated with or without agrin and/or plasmas or IgGs for five hours[13]. After fixation, AChRs were visualized with rhodamine-a-bungarotoxin and the number of aggregates from more than 20 microscopic fields and at least two independent cultures were measured as described (20).

Results

We initially looked for IgG antibodies in five AAAN plasmas and three plasmas from healthy individuals using COS7 cells transfected with rat MuSK constructs (FIG. 1a). The experiments were performed blind. All five AAAN plasmas (e.g., FIG. 1b, AAAN), but none of the healthy control plasmas (e.g., HC), labeled MuSK aggregates on the cell surface at dilutions up to 1:1000. The pattern of immunoreactivity was indistinguishable from labeling observed with antibodies raised against recombinant MuSK in rabbits. (13) Each of the AAAN plasmas recognized the extracellular domains of MuSK, since no immunoreactivity was observed with COS7 cells expressing the transmembrane and cytoplasmic domains only (FIG. 1b, MuSK D). Not all cells expressed MuSK (compare FIG. 1b, AAAN/MuSK and Phase contrast, below), and these non-transfected cells and mock-transfected cells (not shown) did not bind the AAAN IgG antibodies.

Immunoprecipitation experiments confirmed that IgG antibodies in the AAAN plasmas recognized the native MuSK protein. Detergent extracts from MuSK-expressing COS7 cells and from mouse C2C12 myotubes, that express functional MuSK, were incubated with plasmas from two AAAN patients and a healthy control. Antibodies from both AAAN patients, but not from the control, immunoprecipitated bands of 110 kDa that were identified as MuSK by binding of a specific anti-MuSK antibody (FIG. 1c). With each extract, similar-sized bands were immunoprecipitated by a rabbit anti-MuSK serum from parallel extracts (FIG. 1c).

Sera and plasmas from AAAN, anti-AChR positive MG and healthy individuals were then tested in an ELISA. Fragments comprising only extracellular domains of MuSK were expressed in COS7 cells from which these soluble constructs are secreted, and the media were used as a source of the polypeptide antigen. IgG anti-MuSK antibodies, substantially greater than the mean+3SDs of the healthy control values (0.08 OD units) were found in $17/24$ AAAN samples, whereas only borderline or negative values were found in the anti-AChR positive patients (FIG. 2a). Four of the seven negative, compared with only two of the 17 positive samples, were from patients who had received corticosteroid therapy before sampling. Interestingly, in the 11 patients tested in both assays, the OD values for binding of antibodies to MuSK correlated ($p<0.02$) with IgG binding to the human TE671 cell line (which has features of human muscle) as measured previously (8). This suggests that MuSK is the target for AAAN IgG antibodies on the TE671 surface and that the negative values in seven samples are unlikely to be due to a lack of reactivity with rat MuSK Further results with four AAAN plasmas (e.g., FIG. 2b) indicated that the majority of antibodies are directed against the N-terminal sequences (construct Igl-2 in FIG. 1a) and there was little reactivity with the membrane proximal half (construct Ig3-4 in FIG. 1a). We found no evidence of IgM antibodies to MuSK (data not shown), suggesting that the target for the putative non-IgG antibodies reported previously in some of the AAAN patients (15) will still need to be defined.

To investigate functional effects of the MuSK autoantibodies, we examined AChR clustering in myotubes derived from the mouse cell line, C2C12. In the absence of agrin (FIG. 3a upper panels), the control plasma produced very few clusters of AChRs (HC), whereas anti-MuSK positive plasma induced AChR aggregates along the surface of the myotubes (AAAN). A similar antibody-induced induction of AChR-clustering by artificial dimerization of the kinase has previously been reported for rabbit antibodies induced against purified MuSK (13). Strikingly, when agrin was added with the plasmas (FIG. 3a, lower panels), the marked agrin-induced clustering which occurred in the presence of control plasma (HC) was not seen in the presence of AAAN plasma indicating that the anti-MuSK antibodies had inhibited the agrin-induced AChR clustering. Both the clustering (FIG. 3b) and the inhibitory activity (FIG. 3c) were found with each anti-MuSK positive plasmas or IgGs but not with anti-MuSK negative preparations. Since it is currently accepted that agrin does not bind directly to MuSK, but via a hypothetical agrin-binding component called MASC (1,11), we speculate that the antibodies in AAAN patients bind to MuSK in such a manner as to prevent its interaction with MASC. This interaction is known to depend on the N-terminal half of the extracellular domain of MuSK (16) which we find to be the main target for the IgG antibodies in anti AChR autoantibody negative patients (FIG. 2b).

To confirm the specificity of the test for myasthenia gravis, we tested a new group of controls (OND's) from patients with other neurological disorders. (FIG. 4). Only one serum was borderline positive. The relative incidence of MuSK antibodies in AAAN samples, was tested using a second cohort (Cohort 2) of Myasthenia gravis patients who were negative for acetylcholine receptor antibodies. All of these patients had generalized disease and $11/16$ of them were positive for MuSK antibodies.

Antibodies to the fetal isoform of the acetylcholine receptor are found in a few mothers who have had babies born with complete paralysis and fixed joints (22,23). This severe condition is relatively common, but maternal antibodies to fetal acetylcholine receptor are found in only about 1% (Vincent, Dalton, unpublished findings). We asked whether MuSK antibodies might be present in some of these mothers. FIG. 5 shows, in comparison with the previously described results, that six mothers of affected babies out of a total of 200 tested (only 60 shown here) have these antibodies in their serum. This indicates that each of these six mothers has made an autoimmune response to MuSK and suggests that, after transfer of these antibodies across the placenta, they might be involved in causing the babies' condition. Testing for antibodies to MuSK in mothers of babies with muscle paralysis and/or fixed joints might indicate a fetal condition due to maternal antibodies.

To assess how the assay works out in practice, we have begun to compare results from patients with definite SNMG or a strong suspicion of SNMG with those in whom the diagnosis is questionable (? SNMG). FIG. 6 shows that among the first group, which includes cohort 1 and cohort 2, the assay is positive in $39/66$ and among those with a questionable diagnosis the proportion is $6/25$. The assay continues to be negative in healthy individuals.

The ELISA assay used as identified in the above example is difficult to standardize and we have tested an alternative assay, using immunoprecipitation of 5I-MuSK. For this test, the purified extracellular domain of MuSK is iodinated using 125I (carrier free from Amersham as for bungarotoxin in Ref (4,6) or with chloramine T (standard conditions)). The iodinated MuSK is then separated from free 125I by gel filtration. The 125I-MUSK (approximately 50,000 cpm) is then added to 10 microlitres of the patient's serum over night. To immunoprecipitate the patients' antibodies and any 125I-MuSK that is bound by them, excess of a sheep antibody to human IgG is added. The precipitate is centrifuged to form a pellet, washed and counted for radioactivity. The results (FIG. 7) show that healthy controls precipitated less than 1200 cpm, whereas $38/66$ of the SNMG patients precipitated over 1200 cpm, the value rising to 7500 cpm which corresponds to approximately 1 nmole of MuSK precipitated per liter of serum. The assay was also positive in $5/25$ patients with? SNMG.

The results of the ELISA and immunoprecipitation assays were highly correlated (FIG. 8). Most of the sera were positive with both assays or negative with both assays; there were three sera that gave negative results with the immunoprecipitation and positive with ELISA, and two sera that were negative with the ELISA and positive with the immunoprecipitation.

REFERENCES

1. Sanes, J. R., Lichtman, J. W. Development of the vertebrate neuromuscular junction. *Annual Review of Neuroscience* 22: 389-442 (1999).
2. Drachman, D. B. Myasthenia gravis. *New Engl J Med.* 330: 1797-1810 (1994).
3. Saunders, D. B., Andrews, I., Howard, J. F., Massey, J. M. Seronegative myasthenia gravis. *Neurology.* 48: S40-S45 (1997).
4. Vincent, A., Newsom-Davis, J. Acetylcholine receptor antibody as a diagnostic test for myasthenia gravis: results in 153 validated cases and 2967 diagnostic assays. *J Neurol Neurosurg Psychiatry.* 48: 1246-52 (1985).
5. Mossman, S., Vincent, A., Newsom-Davis, J. Myasthenia gravis without acetylcholine-receptor antibody: a distinct disease entity. *Lancet.* 1: 116-119 (1986).
6. Lindstrom, J., Seybold, M. E., Lennon, V. A., Whittingham, S., Duane, D. D., Antibody to acetylcholine receptor in myasthenia gravis: prevalence, clinical correlates and diagnostic values. *Neurology,* 26: 1054-1059 (1976).
7. Brooks, E. B., Pachner, A. R., Drachman, D. B., Kantor, F. S. A sensitive rosetting assay for detection of acetylcholine receptor antibodies using BC3H-1 cells: positive results in 'antibody-negative' myasthenia gravis. *J Neuroimmunol.* 28: 83-93 (1990).
8. Blaes, F., Beeson, D., Plested, P., Lang, B., Vincent, A. IgG from "seronegative" myasthenia gravis patients binds to a muscle cell line, TE671, but not to human acetylcholine receptor. *Ann Neurol.* 47: 504-10 (2000).
9. Vincent, A., Plested, P., Tang, T., Newsom-Davis, J. Serum factors from seronegative myasthenia gravis patients and acetylcholine receptor phosphorylation. *Ann Neurol.* 44: 439A (1998).
10. Valenzuela, D. M. et al. Receptor tyrosine kinase specific for the skeletal muscle lineage: expression in embryonic muscle, at the neuromuscular junction, and after injury. *Neuron.* 15: 573-584 (1995).
11. Glass, D. J. et al. Agrin acts via a MuSK receptor complex. *Cell.* 85: 513-523 (1996).
12. Hopf, C., Hoch, W. Tyrosine phosphorylation of the muscle-specific kinase is exclusively induced by acetylcholine receptor-aggregating agrin fragments. *Eur J Biochem.* 253: 382-389 (1998).
13. Hopf, C., Hoch, W. Dimerization of the muscle-specific kinase induces tyrosine phosphorylation of acetylcholine receptors and their aggregation on the surface of myotubes. *J Biol Chem.* 273: 6467-6473 (1998).
14. Hoch, W., Campanelli, J. T., Harrison, S., Scheller, R. H. Structural domains of agrin required for clustering of nicotinic acetylcholine receptors. *EMBO J.* 13: 2814-2821 (1994).
15. Yamamoto, T. et al. Seronegative myasthenia gravis: a plasma factor inhibiting agonist-induced acetylcholine receptor function copurifies with IgM. *Ann Neurol.* 30: 550-557 (1991).
16. Zhou, H., Glass, D. J., Yancopoulos, G. D., Sanes, J. R. Distinct domains of MuSK mediate its ability to induce and to associate with postsynaptic specializations. *J Cell Biol.* 146: 1133-1146 (1999).
17. Miers, A. K., Havard, C. W. H. Diaphragmatic myasthenia in mother and child. *Postgraduate Med J.* 61: 725-727 (1985).
18. Taylor, S. I., Barbetti, F., Accili, D., Roth, J., Gorden, P. Syndromes of autoimmunity and hypoglycemia. Autoantibodies directed against insulin and its receptor. *Endocrinol Metab Clin North Am* 18: 123-43 (1989).
19. Robertson, S. C., Tynan, J. A., Donoghue, D. J. RTK mutations and human syndromes: when good receptors turn bad. *Trends Genet* 16: 265-271 (2000).
20. Hopf, C., Hoch, W. Heparin inhibits acetylcholine receptor aggregation at two distinct steps in the agrin-induced pathway. *Eur J Neurosci,* 9: 1170-1177 (1997).
21. Hoch W, McConville J, Helms S, Newsom-Davis J, Melms A, Vincent A. Autoantibodies to the receptor tyrosine kinase MuSK in patients with myasthenia gravis without acetylcholine receptor antibodies. *Nat Med,* 7: 365-368 (2001).
22. Vincent A, Newland C, Brueton L, Beeson D, Riemersma S, Huson S, Newsom-Davis J. Arthrogryposis multiplex congenita with maternal autoantibodies specific for a fetal antigen. *Lancet* 346: 24-25 (1995).
23. Riemersma S, Vincent A, Beeson D, Newland C, Brueton L, Huson S, Newsom-Davis J. Association of arthrogryposis multiplex congenita with maternal antibodies inhibiting fetal acetylcholine receptor function. *J Clin Invest,* 98: 2358-2363 (1996).

What is claimed is:

1. A method of diagnosing sero-negative myathenia gravis related to muscle specific tyrosine kinase (MuSK) in a mammal comprising the step of detecting autoantibodies to an epitope of muscle specific tyrosine kinase (MuSK) in a bodily fluid of said mammal.

2. A method of diagnosing sero-negative myathenia gravis related to muscle specific tyrosine kinase (MuSK) in a mammal comprising the step of detecting autoantibodies to an epitope of muscle specific tyrosine kinase (MuSK) in serum, plasma or whole blood of said mammal.

3. A method of diagnosing muscle paralysis and/or fixed joints related to muscle specific tyrosine kinase (MuSK) in a newborn infant, comprising the step of detecting autoantibodies to an epitope of muscle specific tyrosine kinase (MuSK) in a bodily fluid of the infant's mother.

4. A method of diagnosing muscle paralysis and/or fixed joints related to muscle specific tyrosine kinase (MuSK) in a newborn infant, comprising the step of detecting autoantibodies to an epitope of muscle specific tyrosine kinase (MuSK) in serum, plasma or whole blood of the infant's mother.

* * * * *